United States Patent
Brinker et al.

(10) Patent No.: US 6,495,352 B1
(45) Date of Patent: Dec. 17, 2002

(54) SOL-GEL METHOD FOR ENCAPSULATING MOLECULES

(75) Inventors: C. Jeffrey Brinker, Albuquerque, NM (US); Carol S. Ashley, Albuquerque, NM (US); Rimple Bhatia, Albuquerque, NM (US); Anup K. Singh, San Francisco, CA (US)

(73) Assignee: Sandia Corporation, Albuquerque, NM (US)

( * ) Notice: Subject to any disclaimer, the term of this patent is extended or adjusted under 35 U.S.C. 154(b) by 0 days.

(21) Appl. No.: 09/548,638

(22) Filed: Apr. 13, 2000

Related U.S. Application Data

(60) Provisional application No. 60/129,771, filed on Apr. 15, 1999.

(51) Int. Cl.$^7$ .................. C12N 11/14; G01N 33/552; C12Q 1/32; C12Q 1/28
(52) U.S. Cl. ................. 435/176; 435/7.93; 435/26; 435/28; 436/527; 436/815; 436/829
(58) Field of Search ............... 435/7.93, 26, 28, 435/176; 436/527, 815, 829

(56) References Cited

U.S. PATENT DOCUMENTS

| | | | |
|---|---|---|---|
| 5,084,389 A | * | 1/1992 | Lakshmanan et al. |
| 5,200,334 A | | 4/1993 | Dunn et al. .................. 435/182 |
| 6,022,748 A | | 2/2000 | Charych et al. ............ 436/527 |

OTHER PUBLICATIONS

R. Bhatia et al, Chemical Abstract No. 2000: 507056, abstract of Chem. Mater., 12(8), 2434–2441 (2000).*

Singh, A. K., Gupta, A., Mulchandani, A., Chen, W., Bhatia, R. B., Schoeniger, J., Ashley, C.S., Brinker, C.J., "Encapsulation of enzymes and cells in sol–gel matrices for biosensor applications," Proceedings of the International Society for Optical Engineering (SPIE), Dec. 1999, vol. 3858.

Bhatia, R. B., Brinker, C.J., Ashley, C.S., Harris, T.M., "Synthesis of sol–gel matrices for encapsulation of enzymes using an aqueous route," Mater. Res. Sym. Proc., 1998, 519, 183–188.

Bhatia, R., "Synthesis of Sol–Gel Matrices for Encapsulation of Enzymes Using an Aqueous Route," Aug. 1998, MS Thesis, University of New Mexico, Albuquerque, NM.

Ellerby, L.M., Nishida, C.R., Nishida, F., Yamanaka, S.A., Dunn, B., Valentine, J.S., and J. I. Zink, "Encapsulation of proteins in transparent porous silicate glasses prepared by the sol–gel method," Reports, 1992, 1113–1115.

Carturan, G., Campostrini, R., Dire, S., Scardi, V., and De Alteriis, E., "Inorganic gels for immobilization of biocatalysts: Inclusion of invertase–active whole cells of yeast (*saccharomyces cerevisiae*) into thin layers of $SiO_2$ gel deposited on glass sheets," J. of Molecular Catalysis, 1989, 57, L13–L16.

Yamanaka, S.A., Nishida, F., Ellerby, L, Nishida, C.R., Dunn, B., Valentine, J.S., and Zink, J.I, "Enzymatic activity of glucose oxidase encapsulated in transparent glass by the sol–gel method," Chemistry of Materials, 1992, 4(3), 495–497.

Physical and Chemical Aspects of Adsorbents and Catalysts, B.G. Linsen (ed.), 1970, Academic Press, New York, 214–264.

* cited by examiner

Primary Examiner—Mary E. Ceperley
(74) Attorney, Agent, or Firm—Elmer A. Klavetter

(57) ABSTRACT

A method for encapsulating organic molecules, and in particular, biomolecules using sol-gel chemistry. A silica sol is prepared from an aqueous alkali metal silicate solution, such as a mixture of silicon dioxide and sodium or potassium oxide in water. The pH is adjusted to a suitably low value to stabilize the sol by minimizing the rate of siloxane condensation, thereby allowing storage stability of the sol prior to gelation. The organic molecules, generally in solution, is then added with the organic molecules being encapsulated in the sol matrix. After aging, either a thin film can be prepared or a gel can be formed with the encapsulated molecules. Depending upon the acid used, pH, and other processing conditions, the gelation time can be from one minute up to several days. In the method of the present invention, no alcohols are generated as by-products during the sol-gel and encapsulation steps. The organic molecules can be added at any desired pH value, where the pH value is generally chosen to achieve the desired reactivity of the organic molecules. The method of the present invention thereby presents a sufficiently mild encapsulation method to retain a significant portion of the activity of the biomolecules, compared with the activity of the biomolecules in free solution.

21 Claims, 9 Drawing Sheets

SOL-GEL METHOD FOR ENCAPSULATING MOLECULES

This application claims the benefit of U.S. Provisional Application No. 60/129,771, filed Apr. 15,1999.

This invention was made with Government support under Contract No. DE-AC04-94AL85000 awarded by the Department of Energy. The Government has certain rights in the invention.

BACKGROUND OF THE INVENTION

The invention relates generally to a sol-gel method for encapsulation of organic molecules and more particularly, to a sol-gel encapsulation method using an alkali metal silicate precursor.

Sensors using immobilized organic-based receptors are finding ever-increasing application in a wide variety of fields including clinical diagnostics, environmental monitoring, food and drinking water safety, affinity chromatography, enzyme reactors, and illicit drug monitoring. Important in the development of these sensors is immobilization and integration of biological molecules (biomolecules) and other organic molecules in the sensor platform and retention of the functionality of the molecules. Using biological molecules, numerous techniques such as physical adsorption, covalent attachment, entrapment in polymer and inorganic matrices, have been explored over the years to achieve a high yield, reproducible, robust immobilization technique that preserves the biological activity of the recognition molecule without adversely affecting the performance of the transduction component. No single method has emerged as the universal method of choice for each and every application and ongoing efforts strive to optimize these methods to render them adequate for specific applications. Silica host matrices, made by sol-gel process, have been studied as a platform for encapsulation of organic molecules and for biomolecules, such as proteins (including enzymes and antibodies), peptides, nucleic acids and cells. These sol-gel matrices have been chemically inert, hydrophilic, biocompatible, and inexpensive to produce. The matrices can also exhibit superior mechanical strength, enhanced thermal stability, and negligible swelling in solvents compared to organic polymers. The sol-gel matrix can also be tailored to act as a reservoir for water thereby significantly enhancing the ability to maintain the biological activity of entrapped enzymes, antibodies or cells. Biomolecules can find a more stable environment upon encapsulation in a silica host, because the polymeric framework grows around the biomolecule, creating a cage to protect the biomolecule from aggregation and unfolding. Other advantages of silica supports include biocompatibility and provision of resistance to microbial attack by serving as a nanofiltration material.

Sol-gel matrices offer another advantage in that their optical transparency makes them useful for transduction platforms that rely on transmission of light for detection, such as absorbance or fluorescence measurements. Sol-gel films can be made relatively fast and cast as thin layers on sensor surfaces. For silicon oxide/nitride based sensors, such as field-effect transistors or optical fibers, formation of sol-gel films results in minimum alteration in optical, chemical and physical properties of the base material. The hydrophilic nature of silica also allows uninterrupted transport of water and other molecules such as substrates and products of an enzymatic reaction.

In general, sol-gel matrices containing encapsulated organic molecules, and in particular, biomolecules, have been prepared by hydrolysis and condensation of an orthosilicate such as tetramethyl orthosilicate (TMOS) or tetraethyl orthosilicate (TEOS). First, TMOS is partially hydrolyzed in an acidic medium by addition of a controlled amount of water. Next, the biological species is introduced in a suitable buffer to facilitate gelation. The buffer pH is chosen so as to allow the final solution to be close to neutrality in order to avoid denaturation of proteins. However, use of TMOS (or TEOS) as starting material leads to generation of alcohol (e.g., methanol or ethanol), the presence of which in large quantities can be deleterious to biomolecules, such as proteins and cells. In low temperature aging typically used with encapsulation of biological species, the generation of alcohol proceeds for an extended period of time allowing the encapsulated species to denature over time.

Useful would be a method incorporating the advantages of silica sol-gel structures but that does not produce the deleterious alcohols as a by-product.

SUMMARY OF THE INVENTION

According to the present invention, a method is provided to encapsulate molecules by forming a silica sol from a solution of a silicon oxide and alkali metal oxide, such as potassium oxide or sodium oxide, in water, adjusting the pH to a pH value less than approximately 7 to stabilize the silica sol, forming a silica sol matrix solution, adding a solution containing an organic compound to be encapsulated to form a silica sol matrix encapsulating said organic compound, aging said silica sol matrix encapsulating said organic compound, and forming a material selected from the group selected of a thin film and a gel. The ratio of silicon oxide to alkali metal oxide is between approximately 1.5 and approximately 4. Adjustment of the pH to a value less than 7, and generally to a value between approximately 1 and 4, is performed by adding an acid, such as HCl, or by adding a hydrogen-containing ion-exchange compound, such as an acidic cation exchange resin. No alcohols are formed in the method of the present invention.

An important class of organic compounds to be encapsulated include biomolecules, such as peptides, proteins, including enzymes and antibodies, nucleic acids and cells, which require mild processing conditions to preserve the integrity and activity of the biomolecules. Other organic compound classes include, but are not limited to, polysaccharides, carbohydrates, and lipids. Results have shown that certain biomolecules retain greater than 50 percent of their activity compared with the activity of the biomolecules in free solution.

In one embodiment, a silica sol is formed from a solution of a $SiO_2$ and $Na_2O$ in water, the pH is adjusted to a value of approximately 2 to stabilize the silica sol, forming a silica sol matrix solution, a solution containing a biomolecule to be encapsulated is added to form a silica sol matrix encapsulating the biomolecules, the silica sol matrix is aged and either a thin film or gel is formed.

DETAILED DESCRIPTION OF THE INVENTION

The present invention provides a method to encapsulate organic molecules, such as biological molecules (biomolecules), using sol-gel chemistry. Conventional alkali metal silicate processing has been modified to develop a two-step method that makes the processing compatible with addition of organic molecules, such as polysaccharides, carbohydrates, and fluorescent dyes, including rhodamine, and in particular, with biomolecules such as proteins, including enzymes and antibodies, cells, peptides, lipids and lipid structures, nucleic acids, including aptamer, peptide nucleic acids, deoxyribonucleic acid (DNA), and ribonucleic acid (RNA), and other pharmaceutical drug compounds or compounds of therapeutic use (such as doxorubicin) that require moderate processing conditions to preserve the integrity and activity of the biomolecules. In the first step, a low-pH sol is prepared using an alkali metal (such as sodium and potassium) silicate as the silica precursor. The organic molecules are then introduced in a suitable buffer solution and added to the sol to form a doped silica matrix that encapsulates the molecules. Certain biomolecules require that alcohol not be present to retain the integrity and activity of the biomolecules, especially biomolecules such as enzymes and cells. The method of the present invention produces no alcohol and provides a gentle encapsulation that preserves a significant fraction of the activity compared with the activity of the compound in free solution.

Figure 1:
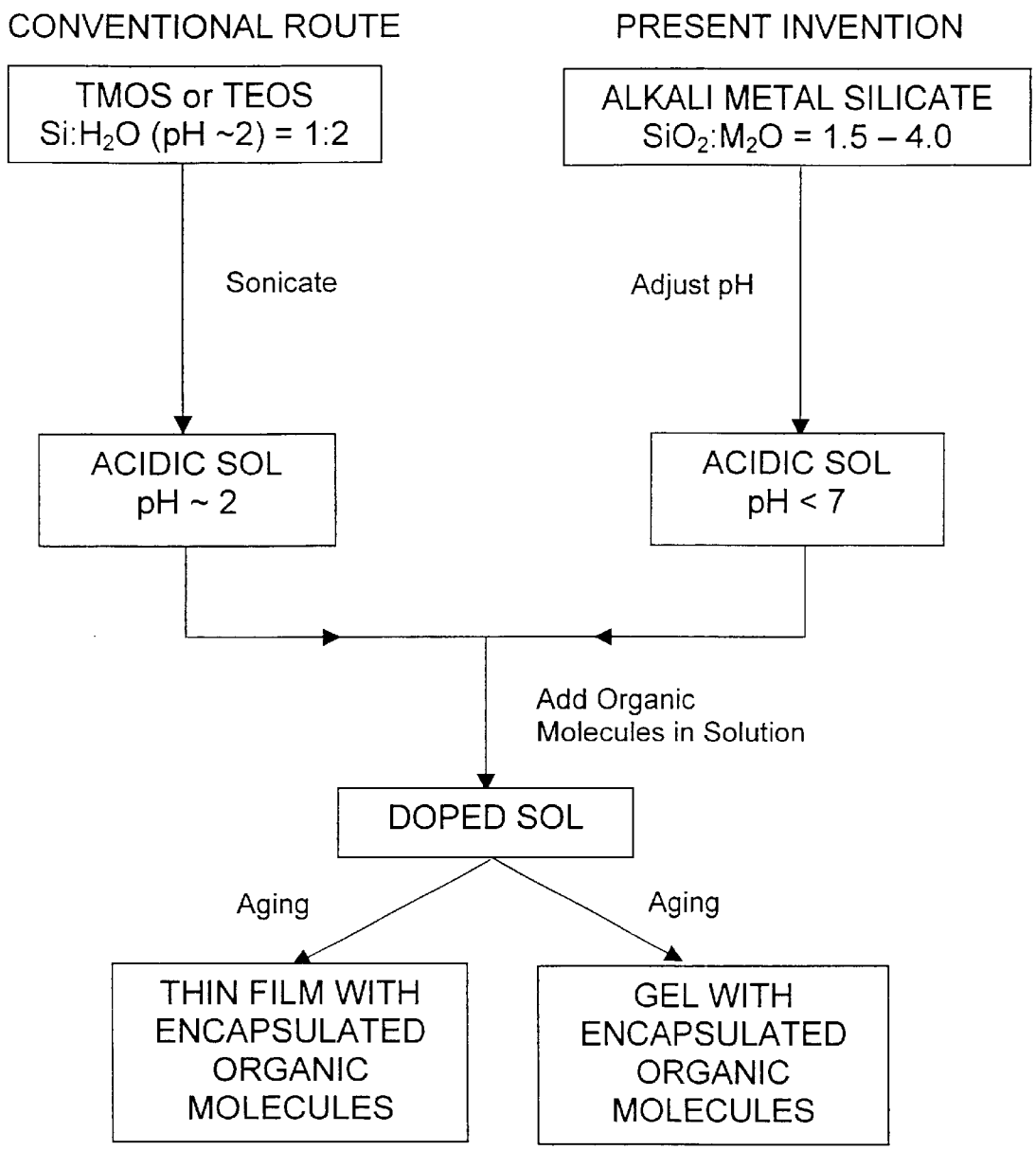
FIG. 1 shows an illustration of the sol-gel method to encapsulate organic molecules.

In the method of the present invention, illustrated in FIG. 1, a silica sol is prepared from an aqueous alkali metal silicate solution. Aqueous sodium and potassium silica solutions are readily available and suitable for use. The alkali metal solution can be prepared from $SiO_2$ and an alkali metal oxide in water. In general, the ratio of the $SiO_2$ to alkali metal oxide ranges from approximately 1.5 to approximately 4. The pH is adjusted to a suitably low value to stabilize the sol by minimizing the rate of siloxane condensation, thereby allowing storage stability of the sol prior to gelation. The value can be any value less than 7; a pH value of 2 is optimal as that is the value of the isoelectric point of silica, with typical values used in the range of approximately 1 to approximately 4. In the absence of this stabilization step, a gel will form before encapsulation can occur. At a pH of approximately 6 to 7, a gel forms almost instantaneously and there is insufficient time for encapsulation to occur. The pH can be adjusted by addition of an acid or by addition of a compound that can ion exchange the alkali metal with hydrogen. Suitable ion-exchange compounds include strongly acidic cation exchange resins such as copolymers, such as a styrene-divinylbenzene copolymer, functionalized with an acid group, such as sulfonic acid. The ion-exchanged compound can optionally be then removed, such as by vacuum filtration or centrifugation. The organic molecules to be encapsulated, generally in solution, are added to the sol matrix. The organic molecules can be added at any stage of the silica sol or gel preparation. Aging can occur through standard techniques such as by storage under controlled temperature conditions and optionally in the presence of additional acid or base. Either a thin film can be prepared, with either a single layer (generally with an average thickness less than approximately 1000 nm) or multiple layers, can be prepared by standard techniques, such as by spin-coating or dip-coating onto a substrate or a gel can be formed with the encapsulated molecules. Depending upon the acid used, pH, and other processing conditions, the gelation time can be from one minute up to several days. In the method of the present invention, no alcohols are generated as by-products during the sol-gel and encapsulation steps. Importantly, the organic molecules can be added at any desired pH value, where the pH value is generally chosen to achieve the desired reactivity of the organic molecules. An important part of the method of the present invention is that the organic molecules can be biological molecules that can be added at pH values compatible with retaining the biological activity and stability of the biomolecules. The method of the present invention thereby presents a sufficiently mild encapsulation method to retain a significant portion of the activity of the biomolecules, compared with the activity of the biomolecules in free solution.

An advantage of using the method of the present invention is that the pore size distribution, porosity, and related physical properties can be tailored by the processing conditions used. For example, in one embodiment encapsulating enzymes, the pore diameters in the gel increased as the final pH increased. The capability to control these physical parameters can be important for applications where transport of analytes or reactants to and from the encapsulated molecules are important. Applications, such as drug delivery, can also require specific pore size distributions to control the transport of the encapsulated molecules in or out of the thin film or gel.

In one preparation, enzymes were encapsulated in silica gels. Two enzymes that were encapsulated were glucose-6-phosphate dehydrogenase (G6PDH) and horseradish peroxidase (HRP). Both HRP and G6PDH are widely used enzymes in bioanalytical applications as they are compatible with a multitude of detection methods including absorbance, fluorescence, chemiluminescence, and electrochemical detection. G6PDH catalyzes the oxidation of glucose-6-phosphate (G6P) in the presence of nicotinamide adenine dinucleotide phosphate ($NADP^+$), which in turn is reduced to NADPH. NADPH can be detected by measuring absorbance at 340 nm or by measuring fluorescence at 465 nm. HRP is a hemeprotein from horseradish that reduces $H_2O_2$ to $H_2O$ while oxidizing a chromophore such as ABTS (azinobis-ethylbenz-thiazoline-sulfonic acid) to generate a colored product. Proteins encapsulated in pores of a sol-gel matrix can exhibit a behavior significantly different than that of free enzyme. In some instances, enzymes only retain 1–2% of their specific activity upon encapsulation in conventional sol-gel supports. In the sol-gel method presented herein, the retention of activity is significantly higher.

First, silica sols were prepared from sodium silicate [(3.25 $SiO_2$:$Na_2O$), $H_2O$] solutions. The ratio of 3.25 was selected to minimize the volume of acid required for neutralization of alkali. Commercially available $SiO_2$:$Na_2O$ solutions with ratios of approximately 1.5 to 4 can be used. Polypropylene containers were used in all steps of sol-gel preparation. 11.5 g of sodium silicate solution was combined with 34 mL of DI water. To this aqueous solution, 15.4 g of strongly acidic cation exchange resin, in this case a styrene-divinylbenzene copolymer with sulfonic functional groups, was added while stirring to bring the pH of the solution to a value of 4. The resin was then removed by vacuum filtration. Hydrochloric acid (0.3 mL of 2M) was added to the filtrate to adjust the pH to 2.0. The resin was regenerated as needed with 500 mL of 4% acid per 100 g of used resin. The low pH of the sol solution minimizes the rate of siloxane condensation allowing it to be stored at room temperature for up to 48 hours before it gels. Longer storage times can be achieved using different reactant material ratios and pH values. The silica sol matrix formed is identified as SSM* in subsequent discussion. A phosphate buffer (1 M, pH 7) containing enzyme at the desired concentration was added to the sol solution in 1:5 (volume) ratio. A pH value of 7 was used for compatibility with the enzyme being encapsulated. After mixing, the solution was quickly transferred to cuvettes or wells of a microtiter plate. Gelation occurred in approximately 5 minutes at room temperature. The sol could also be formed into a thin film. Gels were aged at 4° C. for 24 hours prior to use. Gels used for enzymatic reactions are aged in sealed containers to avoid dehydration of the encapsulated enzymes. Gels containing G6PDH were equilibrated with 0.2 M phosphate buffer (pH 7) by repeated buffer exchange before enzyme activity measurements. Gels containing HRP were equilibrated with 50 mM citrate buffer pH 4.2 prior to measurement of enzyme activity.

The pore size of a biomolecule-doped silica matrix, such as an enzyme-doped silica matrix, needs to meet two requirements. Pores should be large enough to allow unrestricted transport of molecules including buffer ions, substrates and products of biomolecular reaction, and analytes. At the same time, pores should be small enough to prevent leakage of encapsulated macromolecules as well as to exclude hostile agents such as microbes routinely found in the environment. The pore size distribution of the enzyme-doped aerogel matrixes were obtained from desorption experiments. The distribution was measured to be relatively large, with pores as small as 20–30 Å and as high as 800 Å being present. The majority of the pore volume lies in pores having diameters in the range of 120–400 Å, and the mean pore size of the matrix is approximately 200 Å. The pores are sufficiently large to allow free diffusion of small molecules such as substrates and products but small enough to exclude large particles such as bacteria. Assuming a globular structure, HRP and G6PDH have diameters of 64 Å and 88 Å, respectively. Hence, these molecules should be able to diffuse, although at a rate slower than that in solution, in most of the pores of silica matrix. However, no significant leaching of entrapped enzymes was observed over time, or during repeated washes, suggesting that most of the enzyme molecules were sterically confined in smaller pores. Because the protein is added prior to gelation, it is possible that the sol-gel structure is formed around the protein with the protein molecule acting as a template. This is indirectly corroborated by the fact that surfactant micelles and other organic molecules, as small or smaller than proteins, have been successfully used in our laboratory as templates for forming mesoporous sol-gel matrixes. Above pH 4, silanols in a silica matrix are negatively charged and strong adsorption of cationic proteins due to electrostatic attraction can be another mechanism of retention. At pH 7, the final pH during gelation, HRP has approximately no net charge (isoelectric point (pI)=7.2) and G6PDH has a net negative charge (pI=4.6). Hence, neither protein should adsorb strongly to the negatively charged silica matrix. The high ionic strength (1 M phosphate) of the buffer used for gelation should further minimize electrostatic interaction.

High porosity and surface area is another advantage silica matrixes provide over organic polymers. The volume fraction of porosity of a silica matrix prepared by the method of the present invention is as high as 0.92, compared to a porosity of 0.3–0.5 for typical polymeric supports. This can allow one to encapsulate higher amounts of enzymes without significantly reducing their accessibility. The pore size and porosity of a silica matrix is a strong function of pH during gelation. Over the pH range 4 to 7, the lower the pH of the buffer used to gel the network, the lower the pore size and volume fraction porosity. This provides an easily controllable parameter to selectively tune the pore size of a silica matrix.

Figure 2:
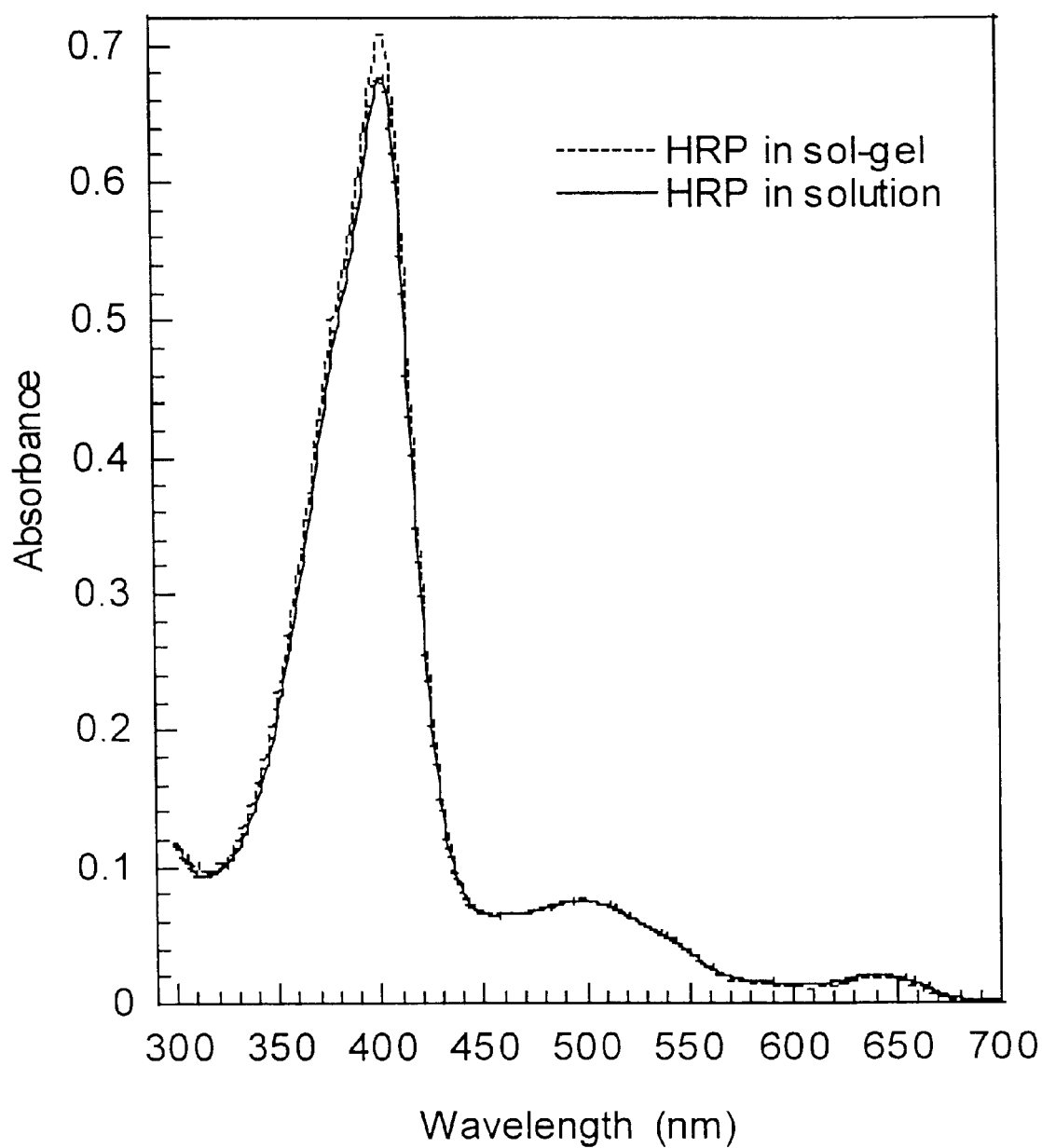
FIG. 2 shows the absorbance of HRP in solution and encapsulated in the sol-gel matrix.

FIG. 2 shows the spectra of HRP in solution and in the silica matrix. The concentration of HRP used was 0.8 mM in both cases. The two spectra are almost identical, indicating that enzyme has not undergone major conformational change upon encapsulation. The peak at 402 nm is due to the presence of the heme group and is quite sensitive to the conformational state of the enzyme. Denaturation of the enzyme can lead to loss of the complexed iron resulting in a decrease in absorbance at 402 nm. The identical spectra of the two forms of enzyme also indicate that the yield of the encapsulation process is close to 100%. In otherwords, the entire amount of enzyme added gets encapsulated. Similar results were observed with encapsulation of G6PDH. We also monitored the loss of encapsulated enzyme in pH 7 phosphate buffer at room temperature over time and did not observe any measurable loss of enzyme over a period of 30 days.

The most important issue in immobilization of a biomolecule is retention of its biological activity upon immobilization. The immobilization or encapsulation process has to be mild enough to retain most of the activity of an encapsulated molecule. For enzymes encapsulated in silica, catalytic activity was determined by measuring the initial rate of product formation.

The results show that HRP lost only 27% of its activity upon immobilization, demonstrating the mildness of the sol-gel process developed in the present invention.

Figure 3:
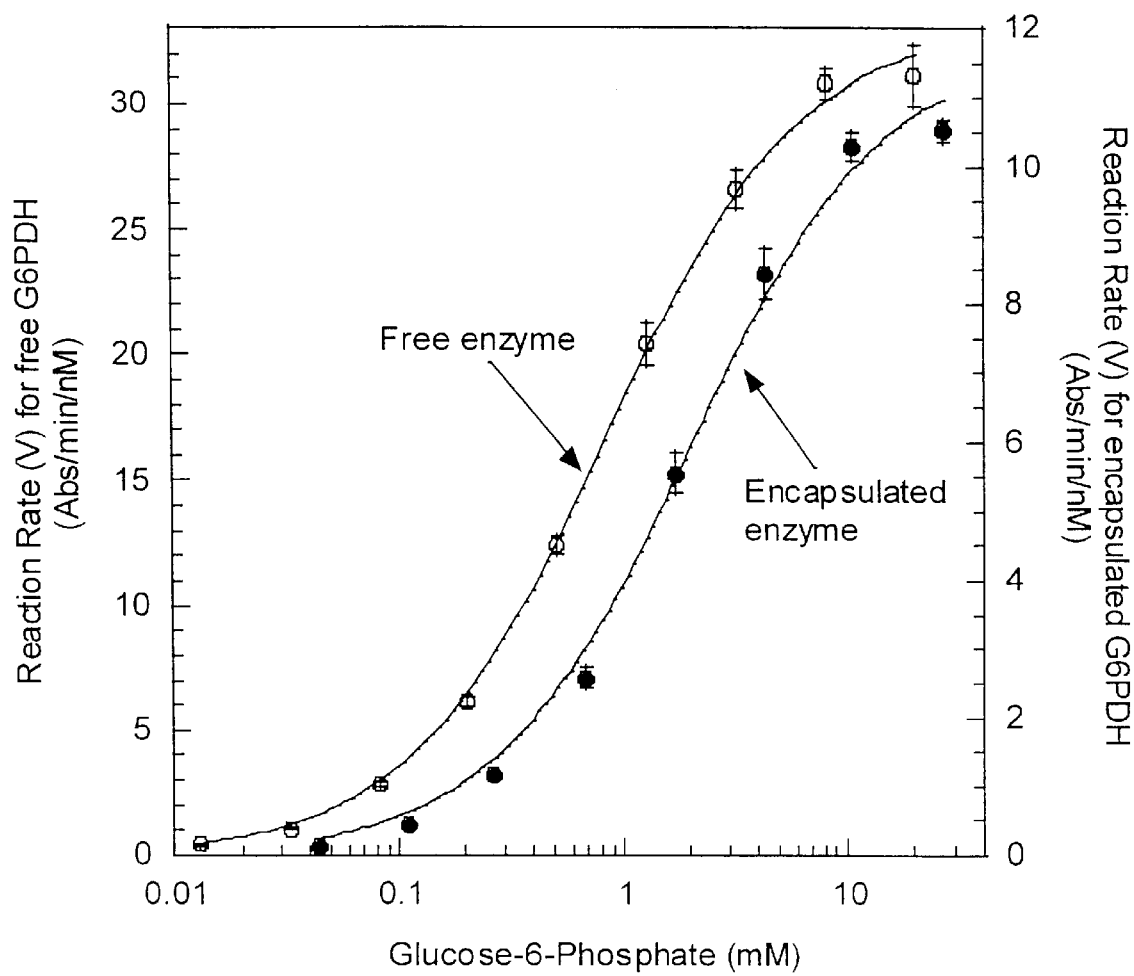
FIG. 3 shows G6PDH reaction rates for the free enzyme and encapsulated enzyme as a function of G6P.
Figure 4:
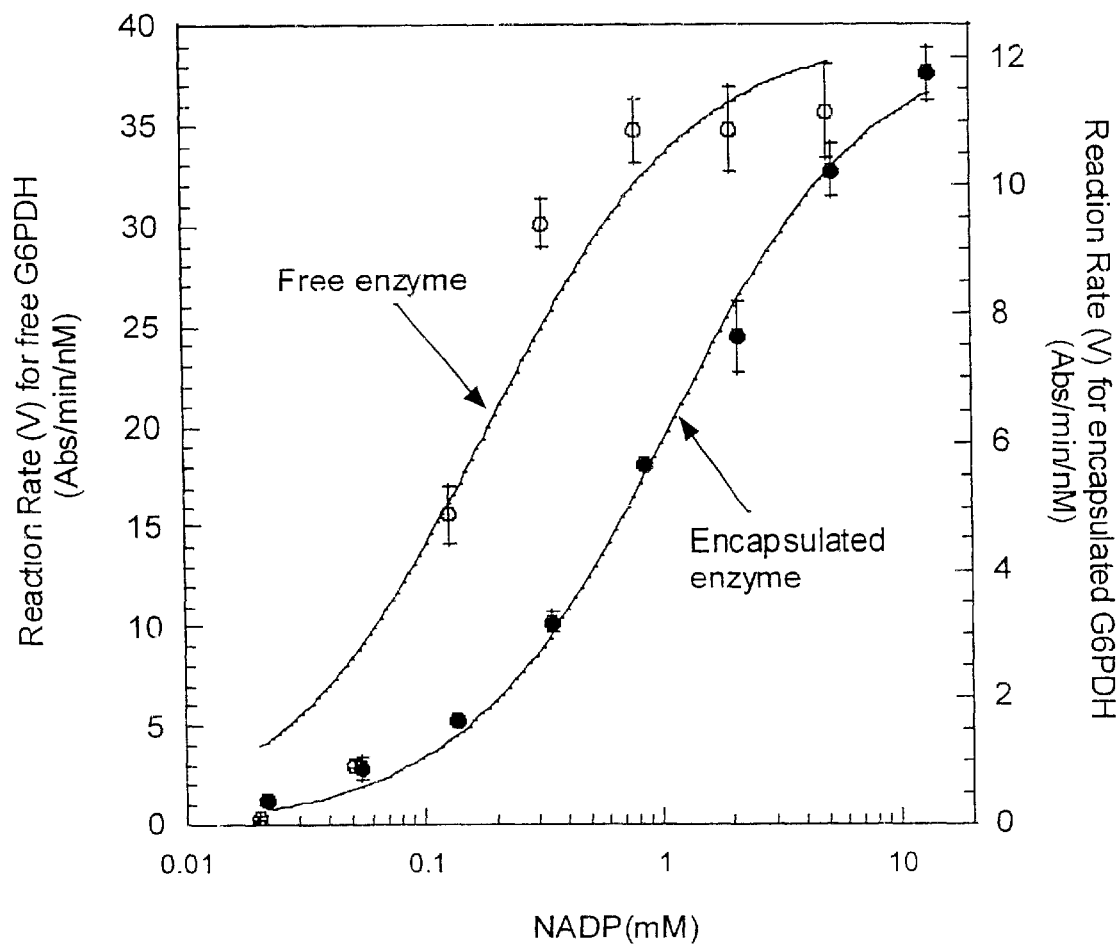
FIG. 4 shows G6PDH reaction rates for the free enzyme and encapsulated enzyme as a function of NADP.

FIG. 3 shows the reaction kinetics of free and encapsulated G6PDH at varying concentrations of NADP$^+$ while keeping G6P concentration constant, and FIG. 4 depicts the kinetics at varying concentrations of G6P while keeping NADP$^+$ concentration fixed. Comparing $k_p$ values for free and immobilized G6PDH, the specific activity of encapsulated enzyme was determined to be 31–36% of that of free enzyme. Comparing specific activities of encapsulated HRP and G6PDH, it can be concluded that HRP retains its specific activity to a greater extent than G6PDH as a result of the encapsulation process. In other words, HRP appears to be a more robust protein than G6PDH with respect to the sol-gel encapsulation process. Most proteins lose their biological activity to some degree during a physical or chemical modification step such as encapsulation. However, each protein, due to its unique tertiary and quaternary structure, responds differently to the modification steps and alterations in its environment. Consequently, in any application requiring immobilized protein, the immobilization process must be optimized for the specific protein with respect to preserving its biological activity. In general, proteins prefer conditions such as physiological pH (close to neutrality), low temperature, and moderate ionic strength. The conditions that adversely affect their activity are high temperature, dilution, and presence of organic solvents. In the sol-gel encapsulation technique presented here, gelation is performed at neutral pH and room temperature in an all-aqueous environment to minimize loss of activity. Using this procedure, both enzymes were able to conserve a significant portion of their activity upon encapsulation.

The concentration of encapsulated enzyme was determined using the Bicinchoninic acid assay. This assay is a colorimetric determination of protein concentration in aqueous solutions. In presence of excess BCA, the color formation (monitored by a spectrophotometer) is directly proportional to the concentration of protein in a sample. Known amounts of a protein are used to form a calibration curve and the amount of protein in an unknown sample is determined from the calibration curve. However, because the Biuret reaction is sensitive to the amino acid content of a protein, the protein used to generate the calibration curve should be the same as the protein whose concentration is being determined. Various concentrations of G6PDH were encapsulated in sol-gel matrixes cast in wells of a microtiter plate. One hundred microliters of free G6PDH ranging in concentrations from 0–1 µM were added to another set of wells to generate a standard curve. The BCA assay was performed according to the manufacturer's instructions. Briefly, reagents were mixed to obtain a final concentration of 0.08% BCA and 2% cupric sulfate in carbonate/bicarbonate buffer. 150 µL of the mixture was then added to the wells containing silica casts, free enzyme or blanks. The plate was incubated at 37° C. for two hours. After two hours, 100 µL of solution was removed from all wells and transferred to another plate. The absorbance at 562 nm with transferred solution was then read using an UV-Vis plate reader.

Figure 5:
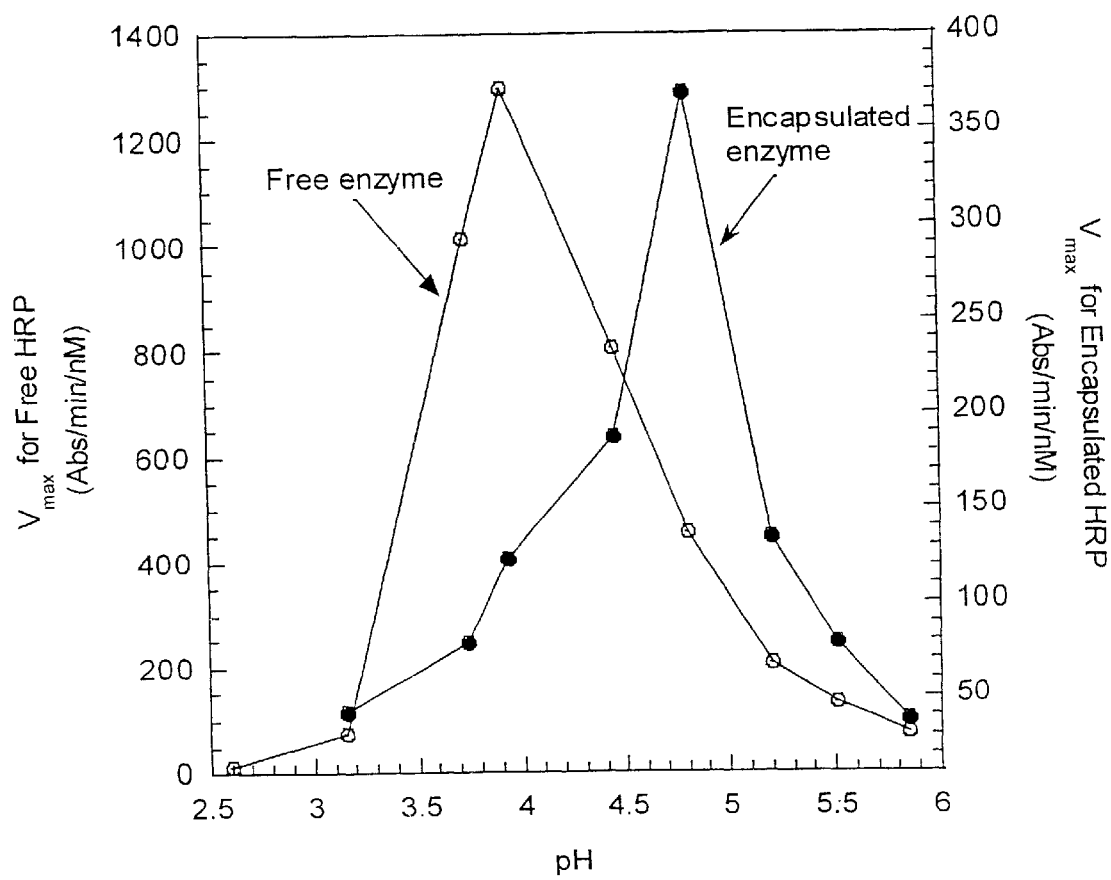
FIG. 5 shows the effect of pH on HRP for both free enzyme and encapsulated enzyme.
Figure 6:
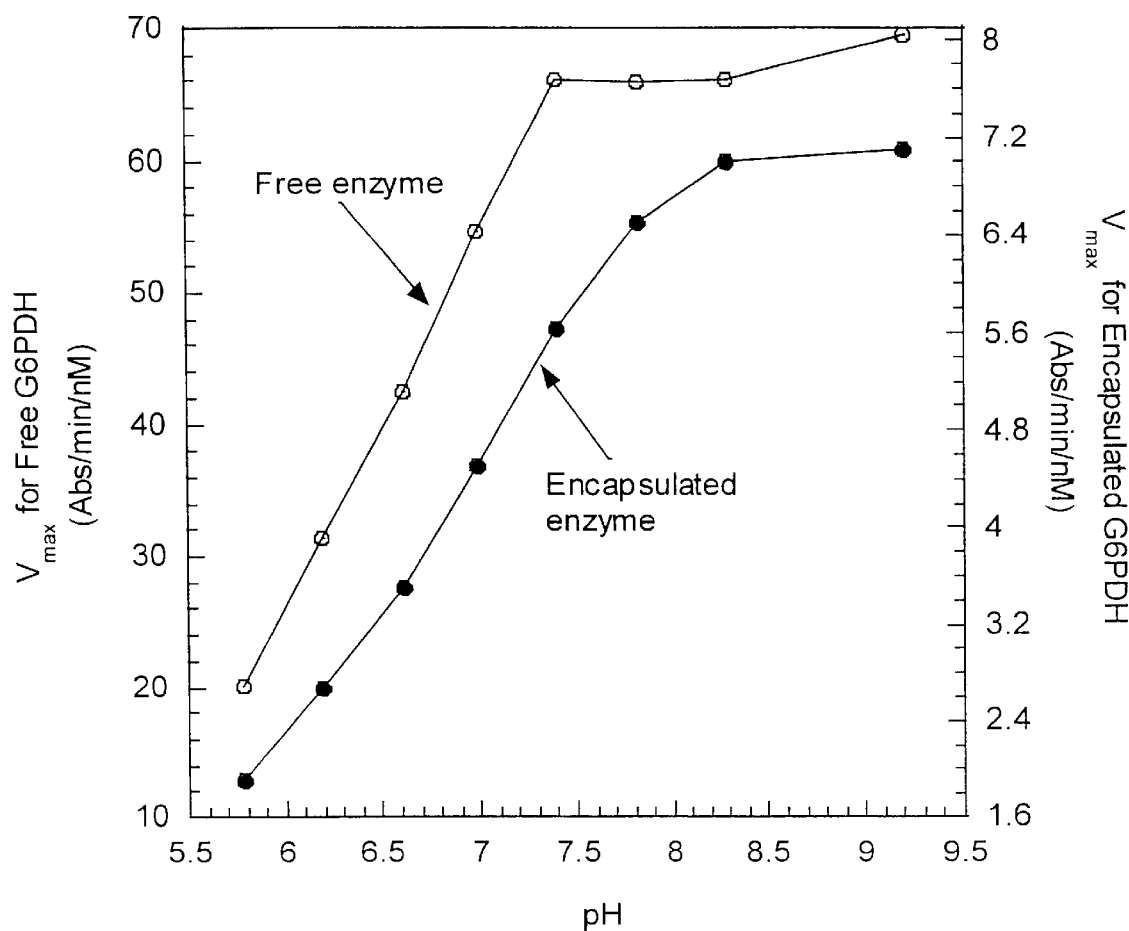
FIG. 6 shows the effect of pH on G6PDH for both free enzyme and encapsulated enzyme.

The pH variations within the pores of a sol-gel, or any support matrix, are important because pH can affect stability as well as biological activity of encapsulated biological molecules. For most enzymes, the catalytic activity is strongly dependent on pH. FIGS. 5 and 6 show the effect of pH on maximal catalytic rate ($V_{max}$) for HRP and G6PDH, respectively, for both free and encapsulated forms of the enzymes. Encapsulated enzymes also exhibited a pH-dependent behavior that is different than that of free enzymes.

In another embodiment, E. Coli cells were encapsulated in the silica sol matrix SSM*, prepared as described previously. The cells remained intact and functional after encapsulation and can be used as biosensors for detection of organophosphates. Organophosphates are toxic compounds that have found extensive use as pesticides, insecticides and potential chemical warfare reagents. Recently, because of environmental, health and national security concerns, significant efforts have been directed toward developing sensitive and portable sensors for these compounds. Organophosphorous hydrolase (OPH), a novel recombinant enzyme, has been shown to effectively hydrolyze a variety of organophosphates and has been to develop direct sensing schemes for them. E. coli strain XL1-Blue was used as the host cell for expression of the OPH enzyme. Plasmid pOPK132 was used for expressing Lpp-OmpA-OPH on the cell surface. Cells bearing the plasmid were grown in 50 ml of LB media buffered to pH 7.0 with 0.017 M $KH_2PO_4$ and 0.072 M $K_2H_2PO_4$, supplemented with 100 mg/ml ampicillin at 370° C. Once the optical density at 600 nm of cell suspension reached 0.5, expression of OPH on the cell surface was induced with 1 mM isopropyl b-D-thiogalactopyranoside (IPTG). After 48 hours of growth, cells were harvested by centrifugation and were resuspended in 1M phosphate buffer. Cells were then encapsulated in the sol-gel matrix as described previously. Care was taken to ensure that the osmolarity of the final buffer was close to physiological level, approximately 150 mM. Gels containing cells were aged for 24 hours at room temperature in presence of excess buffer.

Fluorescence micrographs of fluorescein-labeled E. Coli cells in solution and in sol-gel matrix showed that there was no significant change in the size or shape of the entrapped cells, implying that cells are physically intact after immobilization. The sol-gel process has been shown to be a remarkably gentle method for entrapping macromolecules. The results demonstrate that there is little mechanical or surface stress exerted on the material being encapsulated and this feature has been used advantageously to template molecules.

Figure 7:
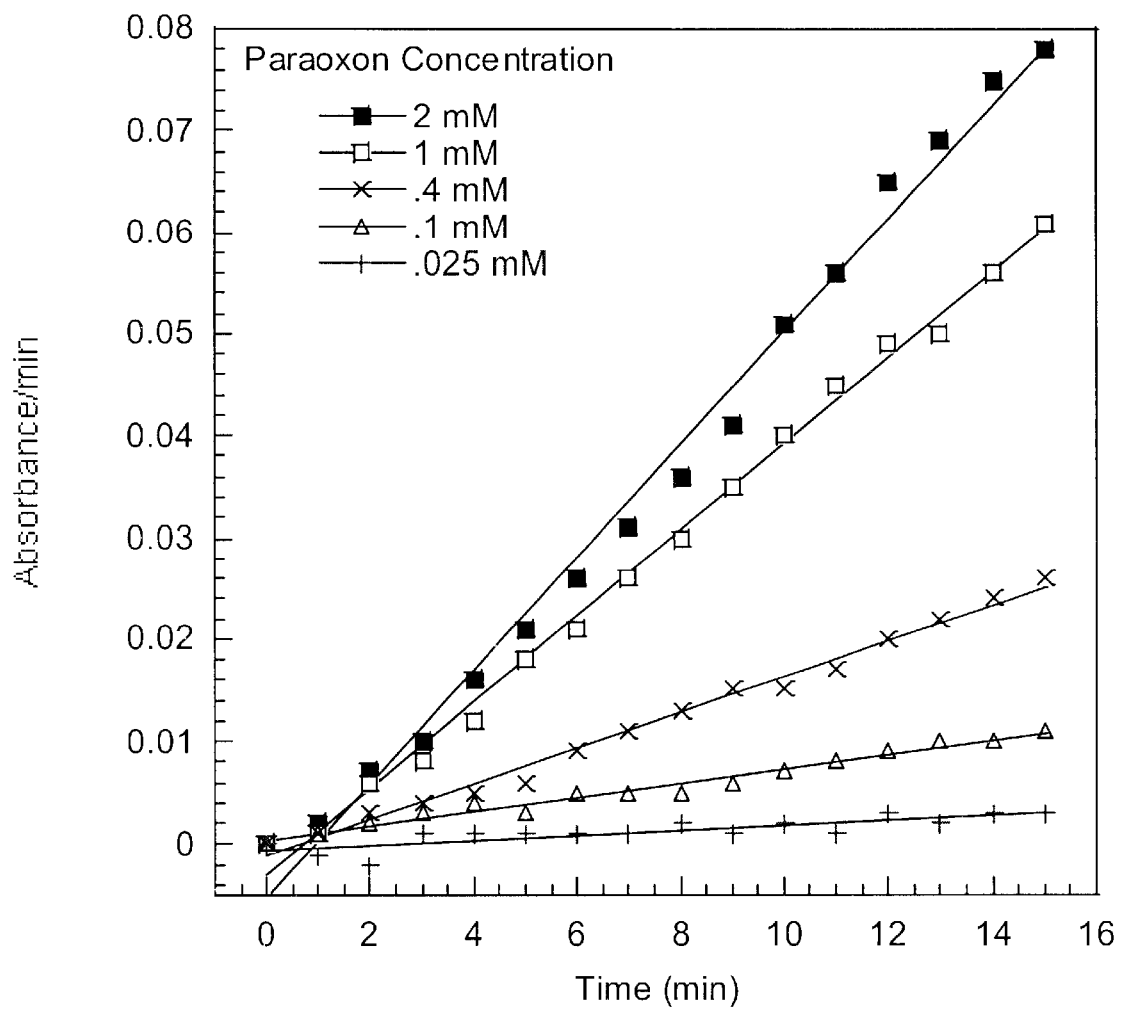
FIG. 7 shows the activity retention of OPH molecules.

The OPH molecules on the surface of immobilized cells retained their activity as depicted in FIG. 7. Paraoxon, an insecticide, was used to determine the activity of immobilized enzyme. Hydrolysis of paraoxon results in production of p-nitrophenol that can be detected by measuring absorbance at 405 nm.

In another embodiment, enzyme-doped and antibody-doped sol-gel matrices were prepared by the method of the present invention for use as dispersible biosensors for explosive materials, and in particular, 2,4,6-trinitrotoluene (TNT). Other explosive materials, such as HDX and RDX, can also be detected. The biosensors can also be used for detection of other organic compounds, such as toxins, illicit drugs, and pharmaceuticals. The sensing is based on a homogeneous immunoassay where the analyte (in this case, TNT) in a sample competes with TNT-enzyme conjugate to bind to a limited number of antibodies present in the solution. The TNT-enzyme conjugate is fully active in the unbound state but when it binds to a TNT antibody, the activity is inhibited. But, the inhibition can be reversed by addition of free TNT. The complex of antibody bound to TNT-enzyme conjugate is encapsulated in a sol-gel matrix together with the substrates for the enzyme. This is the "off" state of biosensor where there is no enzyme activity remaining as all the TNT-enzyme conjugates are bound by antibodies. In the presence of TNT, TNT-enzyme conjugates dissociate from the antibody and become active, catalyzing the conversion of colorless or nonfluorescent substrate into a colored or fluorescent product.

The G6PDH-TNT conjugate was prepared as follows. Trinitrobenzenesulfonic acid (TNBS) was linked to the following spacers—Glycine, 3-aminopropionic acid, γ-amino butyric acid and 6-aminohexanoic acid by reacting 0.76 mmoles of TNBS with 1.52 mmoles of the various linkers. Reaction was carried out at pH 9.5 for 24 hours at room temperature. The product was precipitated by lowering the pH using 2 N HCl. The precipitate was washed extensively with pH 2.0 water and then recrystallized twice in 1:1 Ethanol:water. Dried product (TNP-linker conjugate) was then conjugated to G6PDH by reacting 0.5 mg of G6PDH with TNP-linker conjugate in the presence of 1-ethyl-3-(3-dimethylaminopropyl)carbodiimide (EDC) and N-hydroxysulfosuccinimide (sulfo-NHS) for two hours at room temp in darkness. After reaction, each conjugate was purified by using a size-exclusion column with 10 mM phosphate buffered saline (pH 7.4) as the eluent. Protein concentration and degree of conjugation was estimated by measuring absorbance at 280 nm and 420 nm respectively.

G6PDH-TNT conjugate and TNT antibody were allowed to bind in solution for 15 minutes and then encapsulated in the silica sol matrix SSM*, the preparation of which was described previously, together with the substrate glucose-6-phosphate. The gels were cast in cuvettes or in the wells of a microtiter plate. After aging for a day, sol-gel was exposed to different concentrations of TNT for 2 hours. NAD+ was added and the plate (or the cuvette) was read in an absorbance platereader (or a spectrophotometer).

Figure 8:
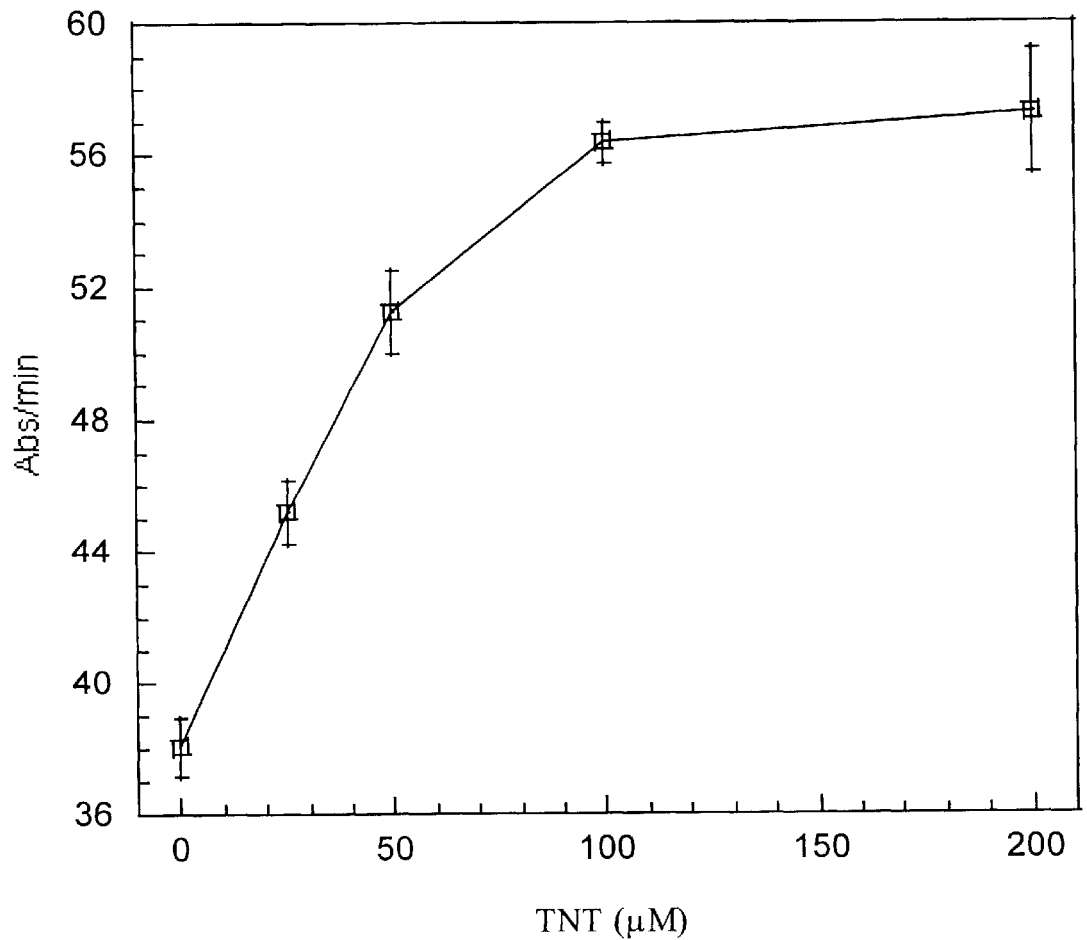
FIG. 8 shows detection of TNT by the method of the present invention.

FIG. 8 shows the results of an immunoassay performed using sol-gel encapsulated reagents for detection of TNT. All the components of the assay namely, the TNT-G6PDH conjugate, the antibody, and glucose-6-phosphate were encapsulated in the sol-gel matrix. Only sample containing TNT and the cofactor NAD+ was added later and the change in absorbance (or fluorescence) of NADH was monitored. The data indicate that a concentration of approximately 10 micromolar (2 ppm) of TNT in solution can be detected.

In another embodiment, silicate sols were prepared from sodium silicate [(3.25 $SiO_2$:$Na_2O$), $H_2O$] solutions without using resin to reduce the pH and stabilize the sol. To prepare 50 ml of the final gel, 11.5 g of sodium silicate solution was combined with 34 ml of distilled, de-ionized water. Instead of adding resin, an alternate procedure was followed where hydrochloric acid was used to prepare the low pH sol. An aqueous solution of sodium silicate was added in small aliquots to 2.0 M HCl (with vigorous stirring) to obtain a $SiO_2$:$H_2O$:HCl molar ratio of 1:50:0.7. An enzyme in buffer solution was then added. Two types of gels were synthesized for the purpose of characterization. For the first type of gel, 0.096 mg glucose oxidase was added to 0.75 ml of pH 7 phosphate buffer (1.0 M). The pH of the sol was then raised by adding the enzyme-buffer solution to 5.25 ml of the sol. Before gelation occurred, the buffered sol was quickly transferred to the corresponding mold. The gels were formed in cuvettes (1 cm×1 cm×2 cm) and in cylindrical polypropylene tubes (1.5 cm×6 cm). Gelation took place in approximately 5 minutes.

A second type of gel was prepared to check bio-activity of the trapped enzymes. This involved the use of a sensor scheme using coupled enzymatic reactions as below

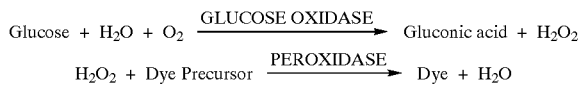

Glucose oxidase and peroxidase, at concentrations of $10^{-8}$ M and $10^{-7}$ M, respectively, were added to 5.5 ml of the phosphate buffer at pH 7. A dye precursor solution of o-dianisidine hydrochloride in phosphate buffer (6 mg/ml) was prepared. The phosphate buffer with enzymes and 0.5 ml of dye precursor solution were added to 42 ml of the sol. The gels were formed in cuvettes and stored at 4° C. All enzyme-buffer additions were made at ice bath temperatures.

Corresponding gels derived from TMOS with the enzymes and dye precursor were prepared for purposes of comparison using conventional sol-gel processing. The cylindrical wet gels, prepared from TMOS and sodium silicate were washed with pH 7 buffer for two hours to desorb any enzyme molecules not bound in the pores of the gel. The solvent in the pores of the gels was then replaced with amyl acetate by pore fluid exchanges. The gels were placed in a pressure chamber that was pre-filled to half its volume with amyl acetate. The chamber was sealed and liquid $CO_2$ (18° C., 950 psi) was allowed to enter the chamber and displace the amyl acetate. The samples were flushed with liquid $CO_2$ 3–4 times to completely replace the pore fluid with $CO_2$. Between the flush cycles, the chamber was sealed to allow soaking in liquid $CO_2$. The temperature was increased to 36° C. over a period of about one hour causing the pressure to rise to 1150 psi, well above the critical temperature and pressure of 31° C. and 1050 psi. The chamber was held above the critical point for approximately 0.5 hour after which time the $CO_2$ was vented to obtain the aerogels.

Figure 9:
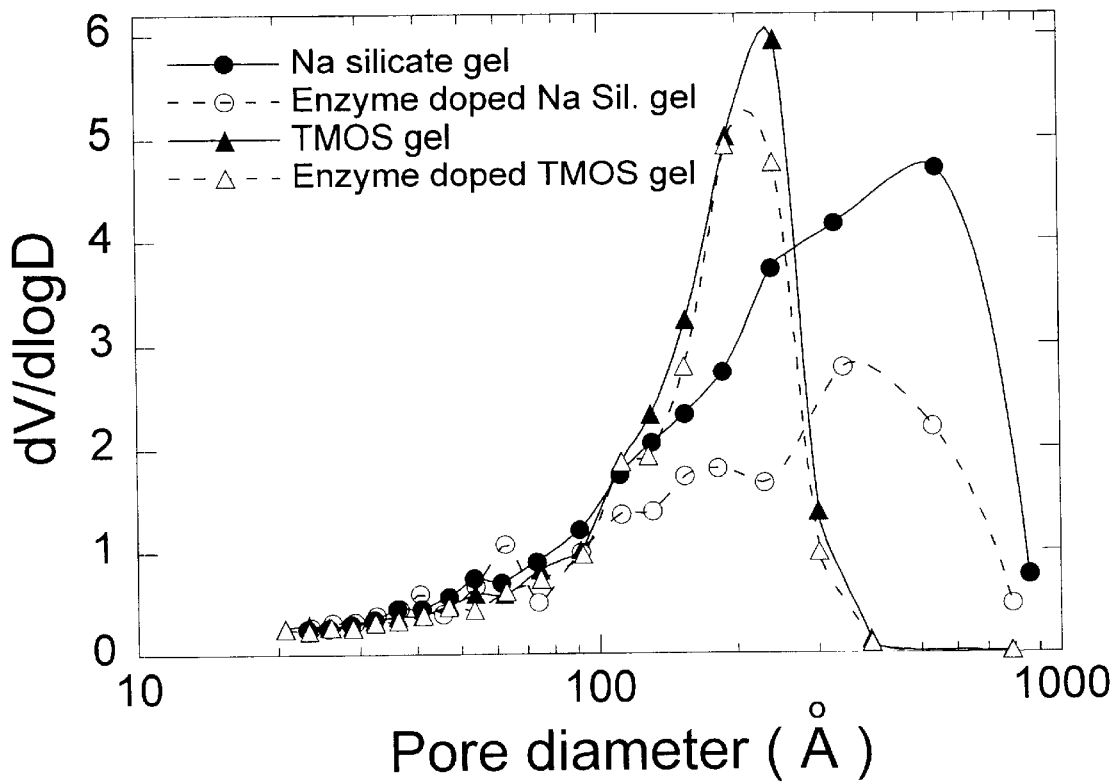
FIG. 9 shows the pore size distribution of aerogels formed by the method of the present invention compared to those of gels made by the conventional TMOS processing route.

FIG. 9 shows the pore size distribution of the aerogels as well as the gels made from the conventional TMOS sol-gel processing route. The figure shows that the gels obtained by the aqueous route have a much broader pore size distribution and higher accessible porosity as compared to the gels obtained from conventional sol-gel processing. The slower sensor response can be explained by diffusional limitations and pore volume limitations that may be imposed in the gels derived from TMOS. In the scheme of coupled enzymatic reactions, the first step involves diffusion of the substrate, i.e., glucose in our system, to the entrapped enzyme. When the substrate binds to the enzyme, an enzyme-substrate complex is formed. The enzyme-substrate complex then results in the product and free enzyme. Further, the product must diffuse to the site of the second enzyme, peroxidase that catalyzes the second reaction to form the dye from the corresponding dye precursors. A larger pore size distribution in aqueous gels allow the dye molecules and enzymes being encapsulated in closer proximity in the aqueous gels as compared to the TMOS gels. Higher accessible porosity and pore volume allows enhanced diffusion of the analytes and greater accessibility to the dye precursor and active enzyme sites. Thus, the differences in the microstructures of the gels can explain faster response in the aqueous gels vs. the gels from conventional sol-gel processing.

Results also show that glucose oxidase activity in the aerogels was retained by observing dye formation upon immersion of the gels in a glucose solution. This result demonstrates that the encapsulated enzyme remains active within the aerogel pores even following supercritical extraction of the solvents from the pores.

The enzyme doped aerogels were then tested for activity using the o-dianisidine calorimetric assay. The enzyme doped aerogels were placed in a solution of glucose to which dye precursor and the peroxidase solution in buffer were added.

The absorption spectra of the enzyme in the silica host matrix as compared to the enzyme in buffer does not show wavelength shifts in peak adsorption or peak broadening. This indicates that the protein has not undergone protein unfolding or changes in structural integrity upon encapsulation.

The invention being thus described, it will be apparent that the same may be varied in many ways. Such variations are not to be regarded as a departure from the spirit and scope of the invention, and all such modifications as would be obvious to one skilled in the art are intended to be included within the scope of the following claims.

We claim:

1. A method to encapsulate molecules, comprising:
   forming a silica sol from a solution of a silicon oxide and alkali metal oxide in water;
   adjusting the pH to a pH value less than approximately 7 to stabilize the silica sol, forming a silica sol matrix solution;
   adding a solution containing an organic compound to be encapsulated to form a silica sol matrix encapsulating said organic compound;
   aging said silica sol matrix encapsulating said organic compound; and
   forming a material selected from the group selected of a thin film and a gel.

2. The method of claim 1 wherein the alkali metal oxide is selected from the group consisting of a potassium oxide and a sodium oxide.

3. The method of claim 1 wherein the silicon oxide is $SiO_2$ and the ratio of $SiO_2$ to alkali metal oxide is between approximately 1.5 and approximately 4.

4. The method of claim 1 wherein the step of adjusting the pH is performed by adding an acid.

5. The method of claim 4 wherein the acid is HCl.

6. The method of claim 1 wherein the step of adjusting the pH is performed by ion-exchanging the alkali metal with a hydrogen-containing ion-exchange compound.

7. The method of claim 6 wherein the hydrogen-containing ion-exchange compound is an acidic cation exchange resin.

8. The method of claim 7 wherein the acidic cation exchange resin is a styrene-divinylbenzene copolymer functionalized with sulfonic acid.

9. The method of claim 6 further comprising the step of removing the ion-exchanged hydrogen-containing ion-exchange compound.

10. The method of claim 1 wherein the organic compound to be encapsulated is a biomolecule selected from the group consisting of proteins, peptides, nucleic acids, lipids, and cells.

11. The method of claim 10 wherein the biomolecule is selected from the group consisting of glucose-6-phosphate dehydrogenase, glucose oxidase, horseradish peroxidase, anti-TNT antibody, and *E. coli* cells.

12. The method of claim 11 wherein the encapsulated biomolecule retains greater than 50 percent of its activity compared with the biomolecule activity in free solution.

13. The method of claim 1 wherein the organic compound to be encapsulated is selected from the group consisting of polysaccharides, carbohydrates, fluorescent dyes, reactants of an enzymatic reaction, a pharmaceutical drug, and compounds of therapeutic use.

14. The method of claim 13 wherein the organic compound to be encapsulated is selected from the group consisting of fluorescein, rhodamine, glucose-6-phosphate, NADP, and doxorubicin.

15. The method of claim 1 wherein the thin film material is formed by a method selected from the group consisting of spin-coating and dip-coating.

16. The method of claim 1 wherein the thin film is formed on a substrate as a sensor.

17. The method of claim 1 wherein the pH is adjusted to a value of between approximately 1 and approximately 4.

18. The method of claim 1 wherein the gel is formed over a period of greater than one hour.

19. A method of encapsulating an organic molecule, comprising:

forming a silica sol from a solution of a $SiO_2$ and $Na_2O$ in water;

adjusting the pH to a pH value less than approximately 7 to stabilize the silica sol, forming a silica sol matrix solution;

adding a solution containing biomolecule to be encapsulated to form a silica sol matrix encapsulating said biomolecules, said biomolecules selected from the group consisting of enzymes, proteins, antibodies, nucleic acids and cells;

aging said silica sol matrix encapsulating said biomolecules; and forming a material selected from the group selected of a thin film and a gel.

20. The method of claim 19 wherein $SiO_2$ and $Na_2O$ are in a ratio of approximately 1.5 to 4.

21. The method of claim 20 wherein the step of adjusting the pH results in a pH value of between approximately 1 and approximately 4.

* * * * *